(12) United States Patent  
Blumenkranz et al.

(10) Patent No.: US 9,295,523 B2  
(45) Date of Patent: Mar. 29, 2016

(54) LOW FRICTION CANNULA SEALS FOR MINIMALLY INVASIVE ROBOTIC SURGERY

(71) Applicant: INTUITIVE SURGICAL OPERATIONS, INC., Sunnyvale, CA (US)

(72) Inventors: Stephen J. Blumenkranz, Los Altos Hills, CA (US); Bruce Michael Schena, Menlo Park, CA (US); Randal Goldberg, Campbell, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 385 days.

(21) Appl. No.: 13/769,036

(22) Filed: Feb. 15, 2013

(65) Prior Publication Data

US 2013/0211423 A1 Aug. 15, 2013

Related U.S. Application Data

(60) Provisional application No. 61/599,288, filed on Feb. 15, 2012.

(51) Int. Cl.  
*A61B 19/00* (2006.01)  
*A61B 17/34* (2006.01)

(52) U.S. Cl.  
CPC ......... *A61B 19/2203* (2013.01); *A61B 17/3462* (2013.01); *A61B 17/3474* (2013.01); *A61B 2017/3441* (2013.01); *A61B 2019/2223* (2013.01); *A61B 2019/2292* (2013.01); *A61B 2019/465* (2013.01)

(58) Field of Classification Search  
CPC ........... A61B 17/3421; A61B 17/3423; A61B 17/3439; A61B 17/3462; A61B 2017/3464; A61B 2017/00557; A61B 19/2203; A61B 2019/2211; A61B 2019/2292; A61B 2019/465  
See application file for complete search history.

(56) References Cited

U.S. PATENT DOCUMENTS

| 4,895,346 A | 1/1990 | Steigerwald |
| 5,295,994 A * | 3/1994 | Bonutti .......................... 606/192 |
| 5,788,676 A | 8/1998 | Yoon |

(Continued)

FOREIGN PATENT DOCUMENTS

WO    WO-2008109408 A2    9/2008

OTHER PUBLICATIONS

International Preliminary Report on Patentability for Application No. PCT/US2013/026519, mailed on Aug. 19, 2014, 9 pages.

(Continued)

*Primary Examiner* — Katherine Rodjom

(57) ABSTRACT

Embodiments of a cannula seal are disclosed. In some embodiments, a cannula seal can include a base portion that engages with a cannula; and a seal portion integrally formed with the base portion that slidebly engages with an instrument shaft such that an insertion frictional force between the seal portion and the instrument shaft for insertion of the instrument shaft is symmetrical and substantially equal with a retraction frictional force.

23 Claims, 15 Drawing Sheets

(56) References Cited

U.S. PATENT DOCUMENTS

| | | |
|---|---|---|
| 2008/0065111 A1* | 3/2008 | Blumenkranz et al. ....... 606/130 |
| 2009/0234293 A1 | 9/2009 | Albrecht et al. |
| 2009/0275898 A1 | 11/2009 | Wenchell |
| 2009/0318868 A1 | 12/2009 | Racenet et al. |
| 2009/0326460 A1 | 12/2009 | Beardsley |
| 2010/0168675 A1 | 7/2010 | Cindrich et al. |
| 2010/0261969 A1 | 10/2010 | Fischvogt et al. |
| 2011/0040255 A1 | 2/2011 | Schweitzer et al. |
| 2011/0087170 A1 | 4/2011 | Insignares et al. |
| 2014/0236177 A1 | 8/2014 | Verner et al. |

OTHER PUBLICATIONS

International Search Report and Written Opinion for Application No. PCT/US2013/026519, mailed on Jun. 3, 2013, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Partial supplementary Search Report for Application No. 13748661.9, mailed on Oct. 21, 2015, 6 pages.

* cited by examiner

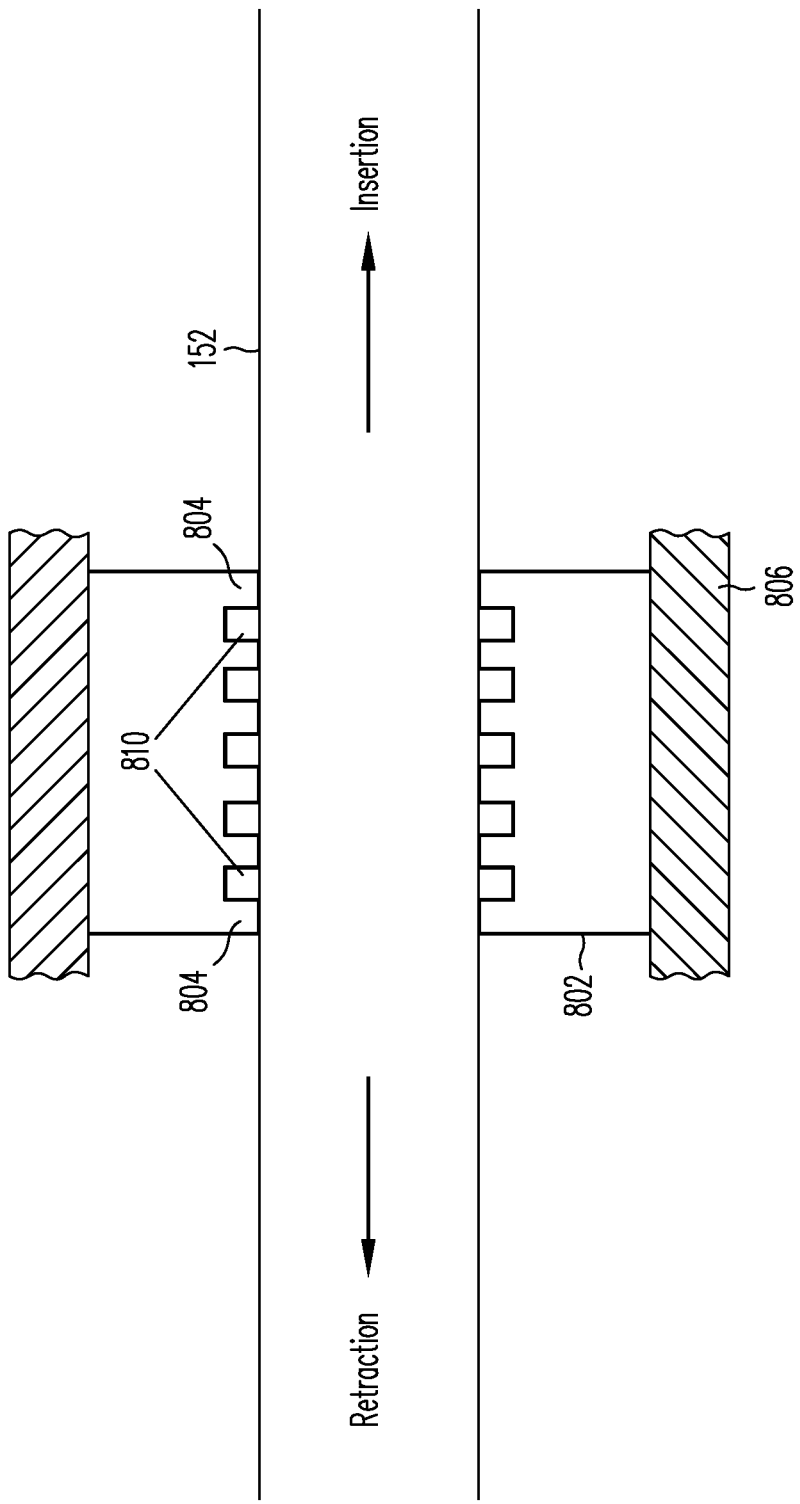

LOW FRICTION CANNULA SEALS FOR MINIMALLY INVASIVE ROBOTIC SURGERY

RELATED APPLICATIONS

This application claims priority to U.S. Provisional Application Ser. No. 61/599,288, filed on Feb. 15, 2012, which is herein incorporated by reference in its entirety.

TECHNICAL FIELD

Embodiments of the present invention are related to seals, and in particular to cannula seals for minimally invasive robotic surgery.

DISCUSSION OF RELATED ART

Surgical procedures can be performed through a surgical robot in a minimally invasive manner. The benefits of a minimally invasive surgery are well known and include less patient trauma, less blood loss, and faster recovery times when compared to traditional, open incision surgery. In addition, the use of robot surgical systems (e.g., teleoperated robotic systems that provide telepresence), such as the da Vinci® Surgical System manufacture by Intuitive Surgical, Inc. of Sunnyvale, Calif., is known. Such robotic surgical systems may allow a surgeon to operate with intuitive control and increased precision when compared to manual minimally invasive surgeries.

In a minimally invasive surgical system, surgery is performed by a surgeon controlling the robot. The robot includes one or more instruments that are coupled to robot arms. The instruments access the surgical area through small incisions through the skin of the patient. A cannula is inserted into the incision and a shaft of the instrument can be inserted through the cannula to access the surgical area. A seal between the cannula and the instrument shaft allows the incision to be sealed during the surgery. Existing cannula seals may have excessive, variable and direction dependent friction that can interfere with fine positioning and force sensing of the instrument tip in the insertion-retraction direction as it contacts surgical patient anatomy.

Therefore, there is a need to develop better performing cannula seals for robotic minimum invasive surgeries.

SUMMARY

In accordance with aspects of the present invention, a cannula seal can include a base portion that engages with a cannula; and a seal portion integrally formed with the base portion that slidebly engages with an instrument shaft such that an insertion frictional force between the seal portion and the instrument shaft for insertion of the instrument shaft is substantially symmetrical and substantially equal with a retraction frictional force. In some embodiments, the frictional forces between the instrument shaft and the cannula seal can be substantially reduced.

A method of symmetrically sealing a cannula can include providing a base portion that attaches to a cannula; and providing a sealing portion integrally formed with the base portion that engages with an instrument shaft such that an insertion frictional force between the seal portion and the instrument shaft for insertion of the instrument shaft is substantially symmetrical with a retraction frictional force.

A surgical system according to some embodiments of the present invention can include a robotic controller; a robot arm coupled to the robotic controller; a surgical instrument coupled to the robot arm and controlled by the robotic controller, the surgical instrument including an instrument shaft and a force sensor; a cannula coupled to the robot arm and receiving the instrument shaft of the surgical instrument; and a cannula seal attached to the cannula and engaging the instrument shaft of the surgical instrument, the cannula seal including a base portion that engages with the cannula and a seal portion integrally formed with the base portion that slidebly engages with the instrument shaft such that an insertion frictional force between the seal portion and the instrument shaft is substantially symmetrical and substantially equal with a retraction frictional force. In some embodiments, the robotic controller executes code that receives force measurements from the force sensor, corrects the force measurements for friction between the cannula seal and the instrument shaft, and transmits corrected force feedback to master tool manipulators on the robot controller.

These and other embodiments are further discussed below with respect to the following figures.

BRIEF DESCRIPTION OF THE DRAWINGS

FIGS. 8A and 8B illustrate cannula seals according to some embodiments of the present invention.

DETAILED DESCRIPTION

Figure 1A:
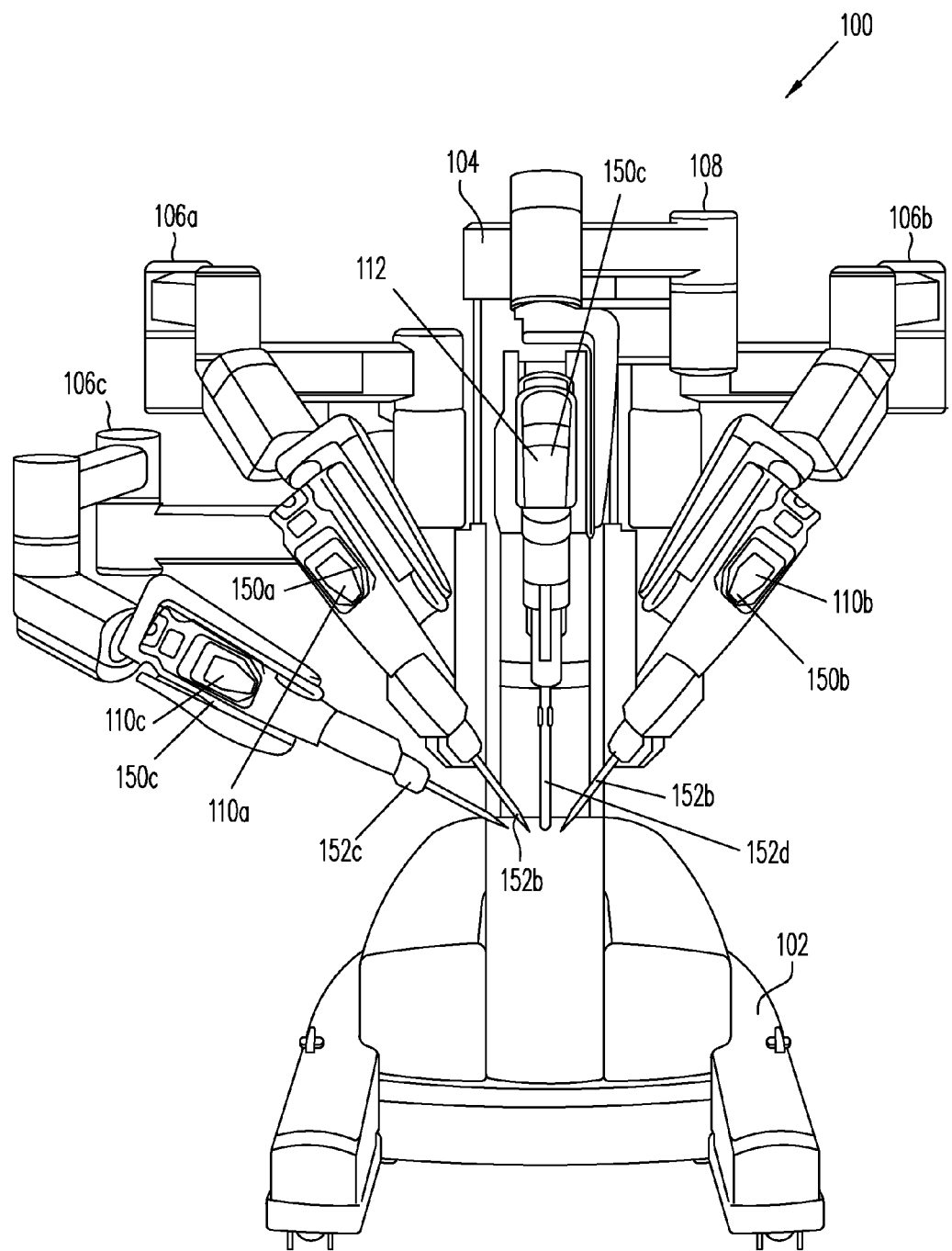
FIGS. 1A, 1B, and 1C illustrate components of an example teleoperated robotic surgical system.

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various mechanical, compositional, structural, and operational changes may be made without departing from the spirit and scope of this description and the claims. In some instances, well-known structures and techniques have not been shown or described in detail in order not to obscure the invention.

Additionally, the drawings are not to scale. Relative sizes of components are for illustrative purposes only and do not reflect the actual sizes that may occur in any actual embodiment of the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Aspects of embodiments of the invention are described within the context of an implementation using a da Vinci® Surgical System (specifically, a Model IS3000, marketed as the da Vinci® Si™ HD™ Surgical System), manufactured by Intuitive Surgical, Inc. of Sunnyvale, Calif. Knowledgeable persons will understand, however, that inventive aspects disclosed herein may be embodied and implemented in various ways, including robotic and non-robotic embodiments and implementations. Implementations on da Vinci® Surgical Systems (e.g., the Model IS3000; the Model IS2000, marketed as the da Vinci® S™ HD™ Surgical System) are merely exemplary and are not to be considered as limiting the scope of the inventive aspects disclosed herein. In particular, some embodiments of the invention assist in better force calculations along a surgical instrument in order to provide force feedback on the controls to a surgeon utilizing the surgical robot.

Figure 1B:
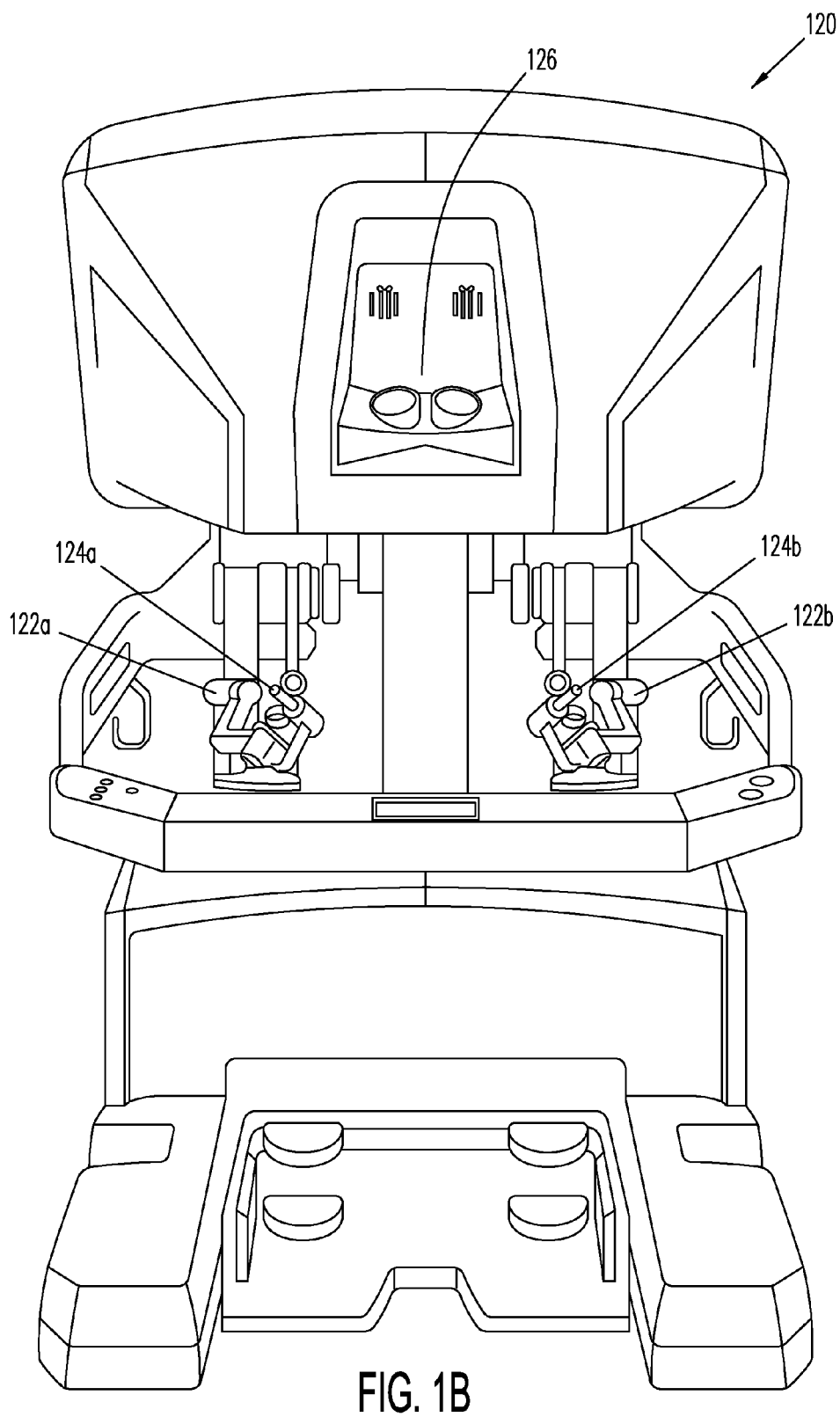
Figure 1C:
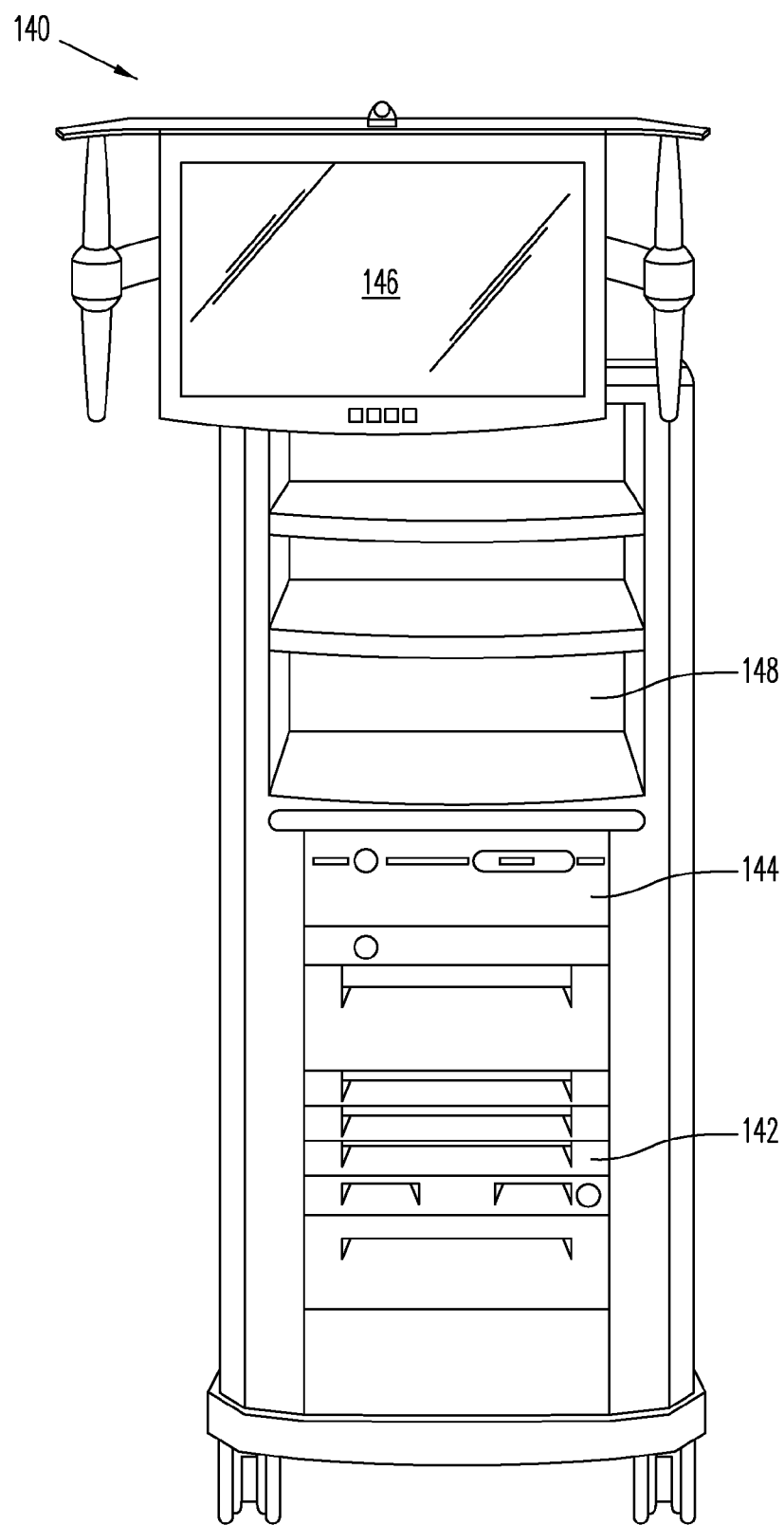

FIGS. 1A, 1B, and 1C are front elevation views of three main components of a teleoperated robotic surgical system for minimally invasive surgery. These three components are interconnected so as to allow a surgeon, with the assistance of a surgical team, to perform diagnostic and corrective surgical procedures on a patient.

FIG. 1A is a front elevation view of the patient side cart component 100 of, for example, the da Vinci® Surgical System. The patient side cart includes a base 102 that rests on the floor, a support tower 104 that is mounted on the base 102, and several arms that support surgical tools. As shown in FIG. 1A, arms 106a, 106b, and 106c are instrument arms that support and move the surgical instruments used to manipulate tissue. Arm 108, for example, can be a camera arm that supports and moves an endoscope instrument 112. Instrument arm 106c can be an optional third instrument arm 106c that is supported on the back side of support tower 104 and that can be positioned to either the left or right side of the patient side cart as necessary to conduct a surgical procedure. FIG. 1A further shows interchangeable surgical instruments 110a,110b,110c mounted on the instrument arms 106a,106b,106c, and it shows endoscope 112 mounted on the camera arm 108. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

As is further illustrated in FIG. 1A, instruments 110a, 110b, 110c, and endoscope 112 include an instrument interface 150a, 150b, 150c, and 150d, respectively, and an instrument shaft 152a, 152b, 152c, and 152d, respectively. In some embodiments, component 100 can include supports for cannulas that fix instruments 110a, 110b, 110c, and endoscope 112 with respect to the cannulas.

Further, portions of each of the instrument arms 106a, 106b, and 106c are adjustable by personnel in the operating room in order to position instruments 110a, 110b, and 110c with respect to a patient. Other portions of arms 106a, 106b, and 106c are actuated and controlled by the surgeon at a surgeon's console 120. Surgical instruments 110a, 110b, 110c, and endoscope 112, can also be controlled by the surgeon at surgeon's console 120.

FIG. 1B is a front elevation view of a surgeon's console 120 component of the da Vinci® Surgical System. The surgeon's console is equipped with left and right multiple DOF master tool manipulators (MTM's) 122a,122b, which are kinematic chains that are used to control the surgical tools. The surgeon grasps a pincher assembly 124a,124b on each MTM 122, typically with the thumb and forefinger, and can move the pincher assembly to various positions and orientations. When a tool control mode is selected, each MTM 122 is coupled to control a corresponding instrument arm 106 for the patient side cart 100. For example, left MTM 122a may be coupled to control instrument arm 106b and instrument 110a, and right MTM 122b may be coupled to control instrument arm 106b and instrument 110b. If the third instrument arm 106c is used during a surgical procedure and is positioned on the left side, then left MTM 122a can be switched between controlling arm 106a and instrument 110a to controlling arm 106c and instrument 110c. Likewise, if the third instrument arm 106c is used during a surgical procedure and is positioned on the right side, then right MTM 122a can be switched between controlling arm 106b and instrument 110b to controlling arm 106c and instrument 110c. In some instances, control assignments between MTM's 122a,122b and arm 106a/instrument 110a combination and arm 106b/instrument 110b combination may also be exchanged. This may be done, for example, if the endoscope is rolled 180 degrees, so that the instrument moving in the endoscope's field of view appears to be on the same side as the MTM the surgeon is moving. The pincher assembly is typically used to operate a jawed surgical end effector (e.g., scissors, grasping retractor, needle driver, and the like) at the distal end of an instrument 110.

In accordance with certain aspects of the present invention, MTM's 122a, 122b can provide haptic force feedback to the surgeon. This force feedback allows the surgeon to more accurately control the MTM's so as to operate the jawed surgical end effectors of instruments 110a, 110b and 110c.

Accurate sensing of forces on instruments 110a, 110b and 110c allows for a reliable force feedback, which allows the surgeon to more accurately control instruments 110a, 110b and 110c.

Surgeon's console 120 also includes a stereoscopic image display system 126. Left side and right side images captured by the stereoscopic endoscope 112 are output on corresponding left and right displays, which the surgeon perceives as a three-dimensional image on display system 126. In an advantageous configuration, the MTM's 122 are positioned below display system 126 so that the images of the surgical tools shown in the display appear to be co-located with the surgeon's hands below the display. This feature allows the surgeon to intuitively control the various surgical tools in the three-dimensional display as if watching the hands directly. Accordingly, the MTM servo control of the associated instrument arm and instrument is based on the endoscopic image reference frame.

The endoscopic image reference frame is also used if the MTM's 122 are switched to a camera control mode. In the da Vinci® Surgical System, if the camera control mode is selected, the surgeon may move the distal end of the endoscope by moving one or both of the MTM's 122 together (portions of the two MTM's 122 may be servomechanically coupled so that the two MTM portions appear to move together as a unit). The surgeon may then intuitively move (e.g., pan, tilt, zoom) the displayed stereoscopic image by moving the MTM's 122 as if holding the image in the hands.

The surgeon's console 120 is typically located in the same operating room as the patient side cart 100, although it is positioned so that the surgeon operating the console is outside the sterile field. One or more assistants typically assist the surgeon by working within the sterile surgical field (e.g., to change tools on the patient side cart, to perform manual retraction, etc.). Accordingly, the surgeon operates remote from the sterile field, and so the console may be located in a separate room or building from the operating room. In some implementations, two consoles 120 (either co-located or remote from one another) may be networked together so that two surgeons can simultaneously view and control tools at the surgical site.

FIG. 1C is a front elevation view of a vision cart component 140 of the da Vinci® Surgical System. The vision cart 140 houses the surgical system's central electronic data processing unit 142 and vision equipment 144. The central electronic data processing unit includes much of the data processing used to operate the surgical system. In various other implementations, however, the electronic data processing may be distributed in the surgeon console and patient side cart. The vision equipment includes camera control units for the left and right image capture functions of the stereoscopic endoscope 112. The vision equipment also includes illumination equipment (e.g., Xenon lamp) that provides illumination for imaging the surgical site. As shown in FIG. 1C, the vision cart includes an optional 24-inch touch screen monitor 146, which may be mounted elsewhere, such as on the patient side cart 100. The vision cart 140 further includes space 148 for optional auxiliary surgical equipment, such as electrosurgical units and insufflators. The patient side cart and the surgeon's console are coupled via optical fiber communications links to the vision cart so that the three components together act as a single teleoperated minimally invasive surgical system that provides an intuitive telepresence for the surgeon. And, as mentioned above, a second surgeon's console may be included so that a second surgeon can, e.g., proctor the first surgeon's work.

During a typical surgical procedure with the robotic surgical system described with reference to FIGS. 1A-1C, at least two incisions are made into the patient's body (usually with the use of a trocar to place the associated cannula). One incision is for the endoscope camera instrument, and the other incisions are for the surgical instruments. In some surgical procedures, several instrument and/or camera ports are utilized to provide access and imaging for a surgical site. Although the incisions are relatively small in comparison to larger incisions used for traditional open surgery, a minimum number of incisions is desired to further reduce patient trauma and for improved cosmesis.

Figure 2:
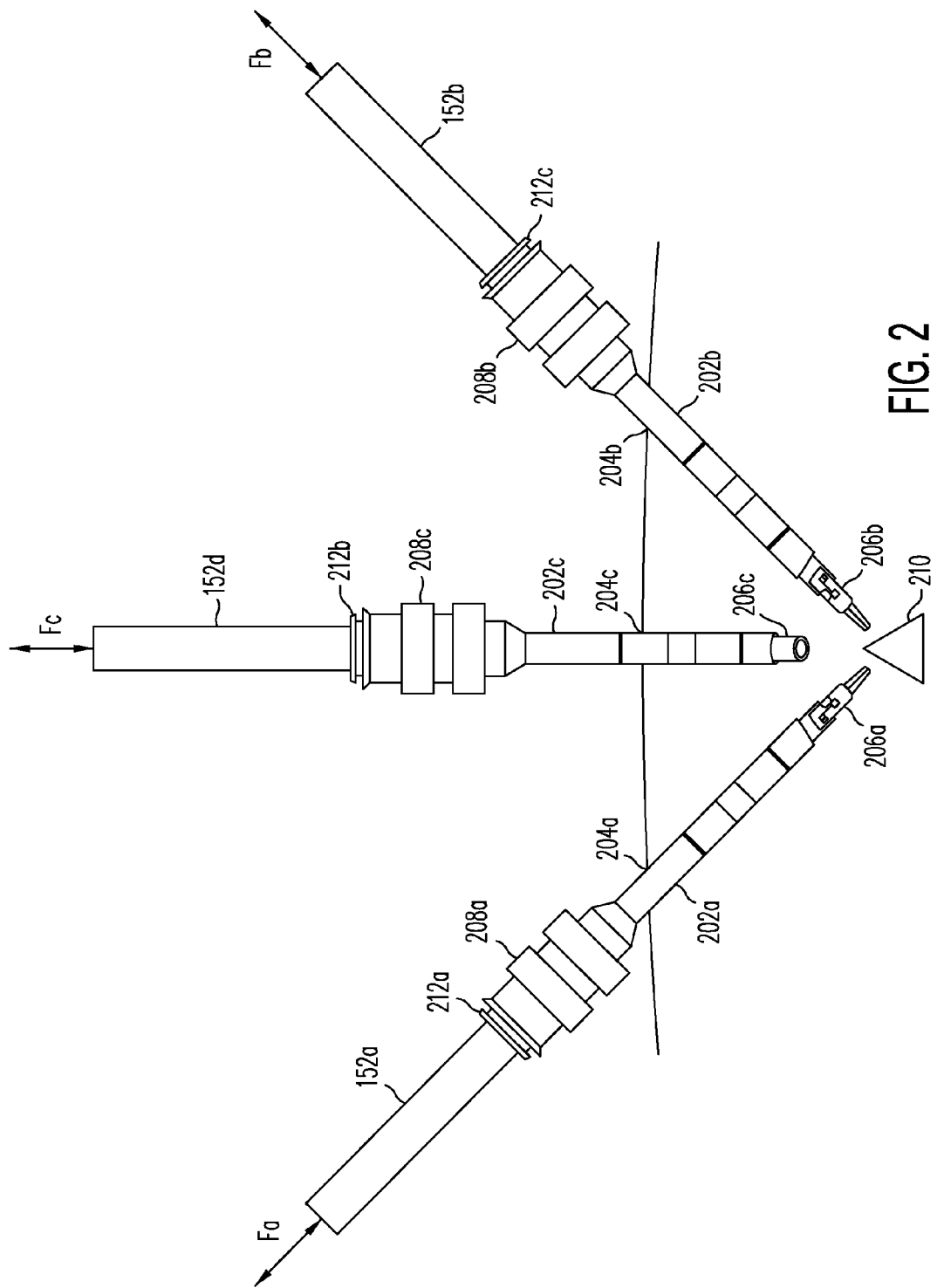
FIG. 2 illustrates cannulas as utilized by the system of FIGS. 1A, 1B, and 1C.

FIG. 2 illustrates utilization of the surgical instrument illustrated in FIGS. 1A, 1B, and 1C. As shown in FIG. 2, shafts 152a, 152b, and 152d pass through cannulas 202a, 202b, and 202c, respectively. Cannulas 202a, 202b, and 202c extend through instrument incisions 204a, 204b, and 204c, respectively. As is shown in FIG. 2, shafts 152a, 152b, and 152d extend through cannulas 202a, 202b, and 202c, respectively. End effectors 206a, 206b, and 206c are attached to shafts 152a, 152b, and 152d, respectively. As discussed above, end effectors 206a, and 206b can be jawed surgical end effectors (e.g., scissors, grasping retractor, needle driver, and the like). Further, end effector 206c is illustrated as an endoscope tip. As shown in FIG. 2, cannulas 202a, 202b, and 202c and shafts 152a, 152b, and 152d are positioned so that end effectors 206a, 206b, and 206c operate in a surgical area 210.

As shown in FIG. 2 cannulas 202a, 202b, and 202c include mounting fittings 208a, 208b, and 208c, respectively, that can be engaged by arms 106a, 106b, and endoscope arm 108, respectively, to allow for very little movement of the instrument end effectors 206a, 206b, and 206c, respectively, as possible. Cannulas 202a, 202b, and 202c further include cannula seal mounts 212a, 212b, and 212c, respectively.

Cannula seals mounted to cannula seal mounts 212a, 212b, and 212c prevent leakage around shafts 152a, 152b, and 152d, respectively. During surgery, particularly if the surgery is abdominal surgery, pressurized $CO_2$ can be utilized to expand the abdomen, allowing for better access to surgical area 210. Further, cannula seals attached to cannula seal mounts 212a, 212b, and 212c prevent leakage of fluids or other materials from the patient.

During the operation, the surgeon sitting at surgeon's console 120 can manipulate end effectors 206a, 206b, and 206c as well as move shafts 152a, 152b, and 152d along force lines Fa, Fb, and Fc, respectively. These force lines represent forces along the insertion/retraction direction (i.e., the direction along shaft 152). Collectively, whether insertion or retraction, this direction may be referred to as the insertion direction.

Figure 9A:
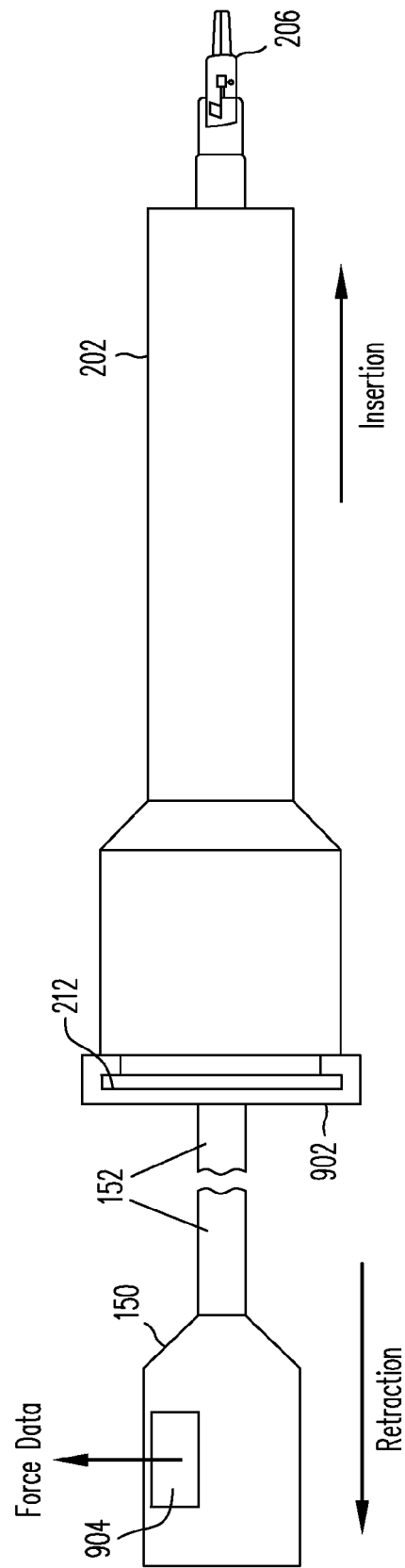
FIGS. 9A and 9B illustrate a force sensing process according to some embodiments of the present invention.

As shown in FIG. 9A, utilizing various force measuring devices 904, the forces on end effectors 206a, 206b, and 206c can be utilized to provide force feedback to the surgeon at console 120, usually through resistance to the surgeon's input at MTMs 122, to allow the surgeon to control the force applied to end effectors 206a, 206b, and 206c. FIG. 9A also illustrates a cannula seal 902 according to some embodiments of the present invention sealing shaft 152 and engaging cannula mount 212.

Effective surgical instrument force feedback utilizes a full 3 dimensional sensing of the forces at end effectors 206 (collectively referring to end effectors 206a, 206b, and 206c). While satisfactory instrument shaft mounted force transducers provide good feedback for the transverse surgical forces applied to patient tissue through wrists and jaws of end effectors 206, wrist actuation cable forces utilized to operate end effectors 206 may prevent accurate sensing of surgical forces in the insertion direction (i.e., the direction along shafts 152 (collectively referring to shafts 152a, 152b, 152c, and 152d). As a result, insertion direction forces are typically sensed at the back of surgical instruments 110 (collectively referring to surgical instruments 110a, 110b, 110c, and endoscope 112) at instrument interface 150 (collectively referring to instrument interfaces 150a, 150b, 150c, and 150d) or on arm 106 (collectively referring to arms 106a, 106b, and 106c or endoscope 112). In those cases, the frictional forces of shaft 152 sliding through cannula seals 902 mounted to cannula seal mount 212 (collectively referring to cannula seals mounts 212a, 212b, and 212c) becomes important, especially if that frictional force varies with direction (insertion or retraction), or velocity of shaft 152 through seal 212. In the discussion below, unequal insertion direction forces will be referred to as asymmetric while equal insertion and retraction forces will be referred to as symmetric. Cannula seal features in sliding contact with an inserted instrument shaft will also be referred to as symmetric when similar features face in opposite directions along the insertion direction or when such features do not point either way. Some embodiments of the present invention include cannula seal 902 that substantially reduces or eliminates the directional or velocity dependence in the shaft seal frictional force measured by the force sensing devices, and therefore allow for more accurate feedback of forces to the operating surgeon. In some embodiments, cannula seal 902 may include a pressurized seal where the frictional forces along the insertion direction are substantially zero.

Cannula seals have taken a number of forms including simple unidirectional compliant lip seals, tri-cuspid or multi-cuspid radial leaf seals, and spirally stacked overlapping and/or folded seal leaves akin to a traditional camera lens iris. Each of these types of seals have asymmetric construction which causes unequal seal frictional force depending on the direction of motion.

Figure 3A:
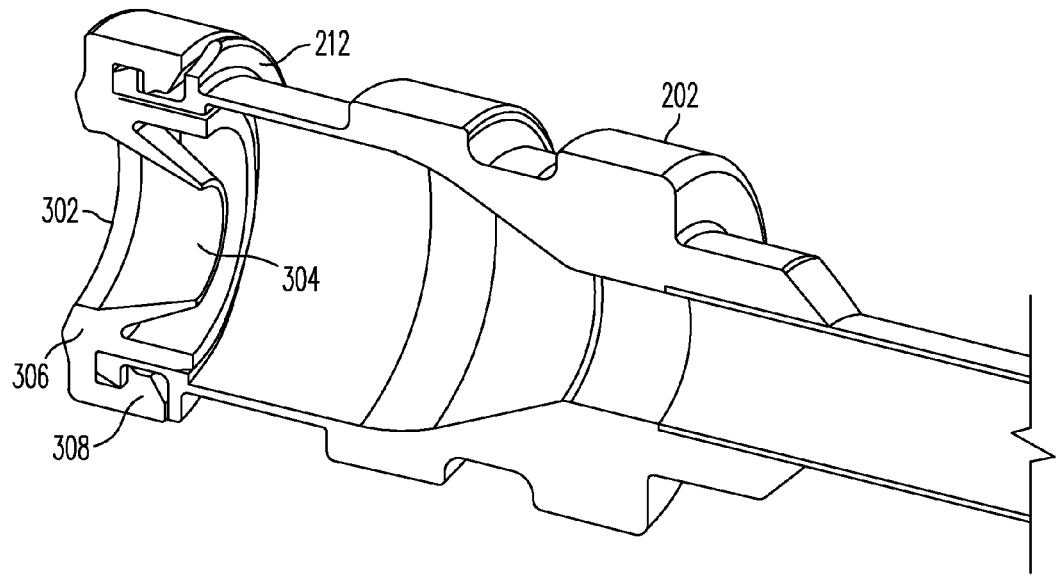
FIGS. 3A and 3B illustrate a conventional cannula seal.
Figure 3B:
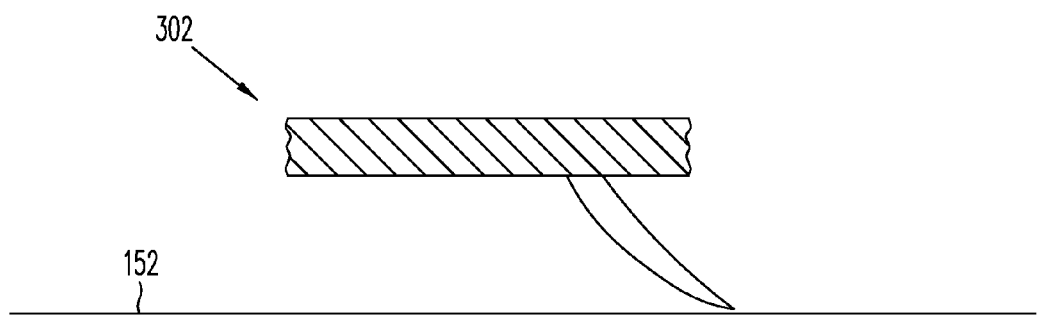
Figure 3B:
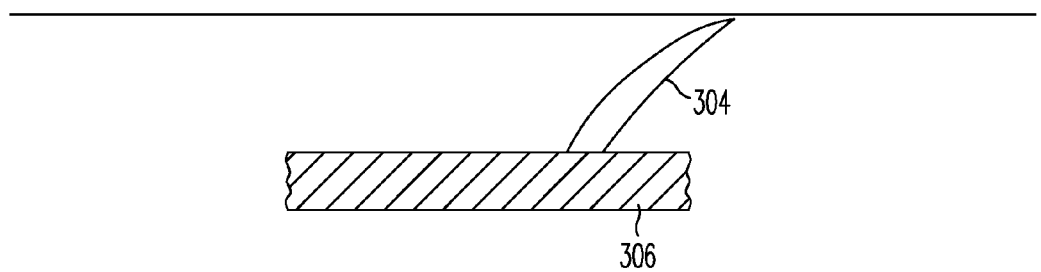

FIGS. 3A and 3B illustrate a conventional cannula seal 302. As shown in FIG. 3A, cannula seal 302 includes a base portion 306 and a retaining portion 308. Base portion 306 is attachable to cannula 202 at cannula seal mount 212 and is held in place by retaining portion 308, which is integrally formed with base portion 306. Retaining portion 308 also provides for sealing against cannula seal mount 212.

Further, cannula seal 302 includes a lip 304 that seals around shaft 152. FIG. 3B illustrates lip 304 sealing around shaft 152. As is illustrated in FIGS. 3A and 3B, lip 304 is asymmetric and is oriented in the insertion direction. Thus, shaft 152 will experience a different frictional force based on direction of motion. As is illustrated in FIG. 3B, lip 304 is oriented in a direction that facilitates motion of shaft 152 the insertion direction. However, in the retraction direction, friction with shaft 152 compresses lip 304 about shaft 152 causing a much higher frictional force. In some cases, the ratio in force between insertion and retraction of shaft 152 can be a factor of about 1.5.

In some cases, especially with abdominal surgery, the direction of 11p 304 assists in sealing against insufflation pressure. In abdominal surgery, pressurized $CO_2$ is provided into the abdomen by an insufflation system in order to expand the abdomen. $CO_2$ utilized in the insufflation system is typically supplied by a pressurized $CO_2$ tank and a regulator. The $CO_2$ pressure in the abdomen will load lip 304 by providing a force that pushes lip 304 more firmly against shaft 152.

Some other cannula seals have two transversely opposing lips like a shortened version of an oboe reed. Yet other seals have a simple compliant circular hole in a diaphragm. In this case, the deflection direction of the seal inverts, the result being that the seal lip faces in the direction opposite where it started, when motion of the shaft through the seal reverses direction, causing further uneven insertion friction force effects. Still other designs rely on an open compliant hole with a rigid plastic door that is pushed aside when the instrument shaft pass through the seal. In this case, the hinge direction of the door exerts asymmetric direction dependent friction forces on the instrument. In every case of existing seals, the forces are excessive, direction dependent, and vary too much with operating conditions to permit motion direction based subtraction of the expected friction forces from sensed forces to null out the frictional effects. The expected friction force contribution may be based on experimental measurements. Therefore, utilizing these seals, the frictional force provides for unreliable force feedback to the surgeon.

Other than the application of lubricant, this problem has not been addressed. Some manufacturers of laparoscopic cannula seals provide a separately packaged pouch of lubricant such as silicone or purified (white mineral oil based) petroleum grease for optional use or pre-coat the seal with such a grease. Silicone or other rubber materials utilized as a seal have a relatively high dry coefficient of friction. Grease lubricants help but do not sufficiently reduce seal friction and may wipe off during a procedure so that the friction varies with time. Grease lubricants also do not equalize the direction dependent forces due to asymmetric seal lip design. Therefore, addition of lubricating materials alone does not significantly help with the asymmetric frictional forces applied when the instrument shaft is moved through a seal.

In some embodiments, the noise limited force sensitivity of a transverse instrument force transducer allows measurement of forces significantly lower than the frictional forces on existing cannula seals. Therefore, the combined effect of all parasitic insertion forces on instrument 110 between a shaft face 152 and cannula seal 902 may be greater than the transverse force transducer sensitivity. It may be possible to improve the transverse force sensitivity further in the future, resulting in a need for a similar improvement in the force sensitivity in the axial direction. Greased seals in combination with present seal designs cannot accomplish the sensitivity needed to provide for reliable force feedback to the surgeon.

Experimental coating of existing molded silicone rubber seals with a dry lubricant parylene managed to reduce the friction between the shaft and the seal by a factor of approximately 4 as opposed to the uncoated seal. The force can be measured with a handheld force gauge. However, the asymmetric nature of the friction caused by conventional seal lips causes a difference in the friction depending on the direction of motion of the shaft through the seal. This asymmetric nature detrimentally affects the ability of the force applied at the effector to be determined by the surgeon.

In particular, in order to provide for a highly reliable indication of the force along shaft 152, both in insertion and retraction, it is desirable that the frictional force between cannula seal 902 attached to cannula seal mount 212 be as symmetric as possible with respect to direction of motion and as uniform as possible during motion. In that case, an estimate of the frictional force can be subtracted from the insertion direction forces measured by a sensor. It is also desirable that the frictional force be as low as possible in order to minimize any remaining error in the improved estimate of the insertion direction surgical force on patient tissue obtained by subtracting the estimated friction force from the sensor measured force.

Figure 4A:
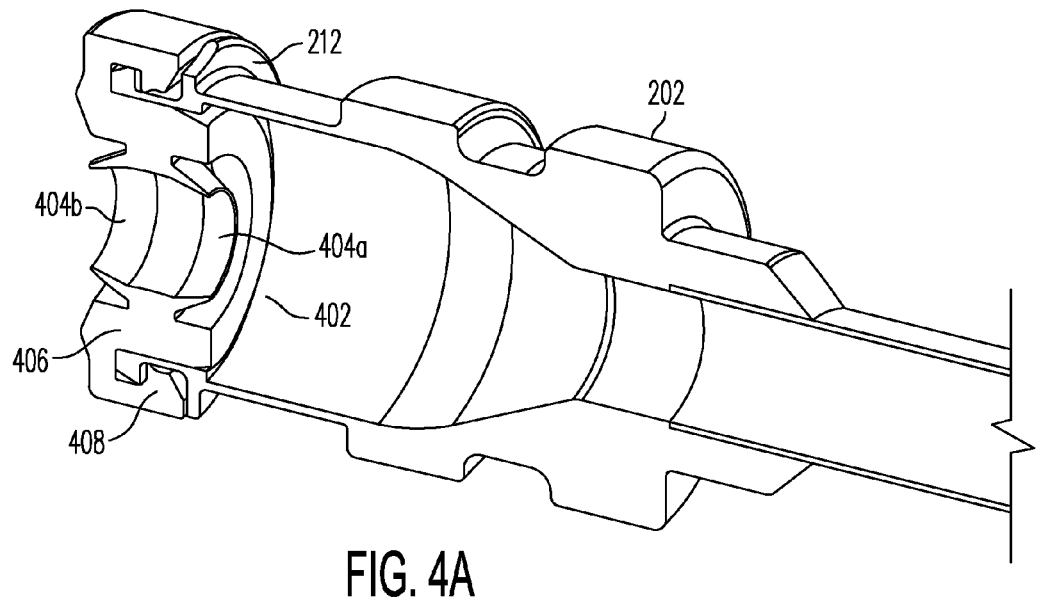
FIGS. 4A and 4B illustrate a cannula seal according to some embodiments of the present invention.
Figure 4B:
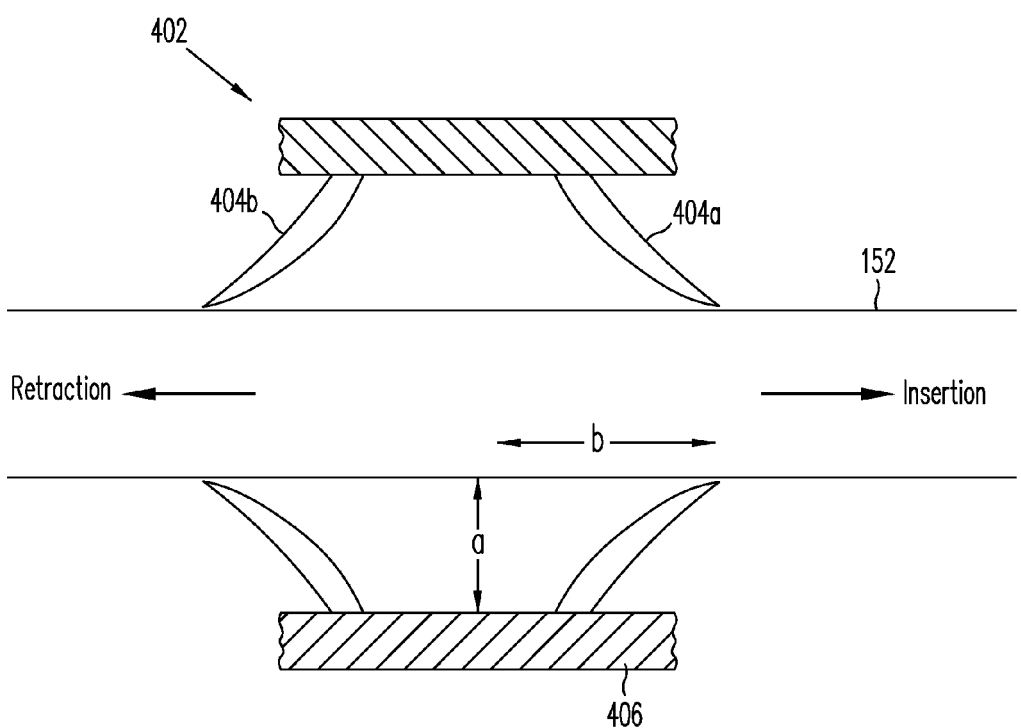

FIGS. 4A and 4B illustrate a cannula seal 402 that can be utilized as cannula seal 902 according to some embodiments of the present invention. As shown in FIG. 4A, cannula seal 402 includes base portion 406 and a sealing portion foamed of lips 404a and 404b. Base portion 406 may include a feature 408 that engages seal retainer 212 of cannula 202. In the embodiment of seal 402 illustrated in FIGS. 4A and 4B, sealing portion lips 404a and 404b are integrally formed, symmetric oppositely oriented lips that seal around shaft 152. As shown in FIG. 4B, lips 404a and 404b are oriented such that lip 404a provides relatively low friction (lower than lip 404b) in the insertion direction and lip 404b provides relatively low friction (lower than lip 404a) in the retraction direction. In that fashion, insertion of shaft 152 and retraction of shaft 152 both experience substantially the same frictional force from seal 402. In that fashion, the insertion/retraction force for shaft 152 can be better calculated.

Figure 6A:
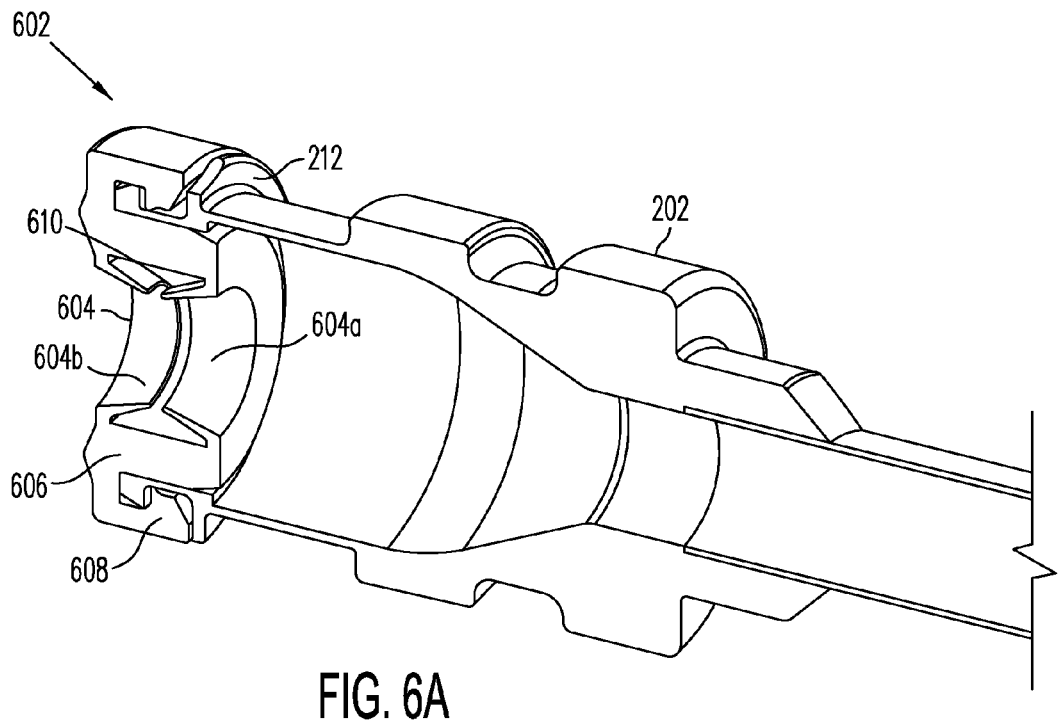
FIGS. 6A, 6B, and 6C illustrate cannula seals according to some embodiments of the present invention.
Figure 6B:
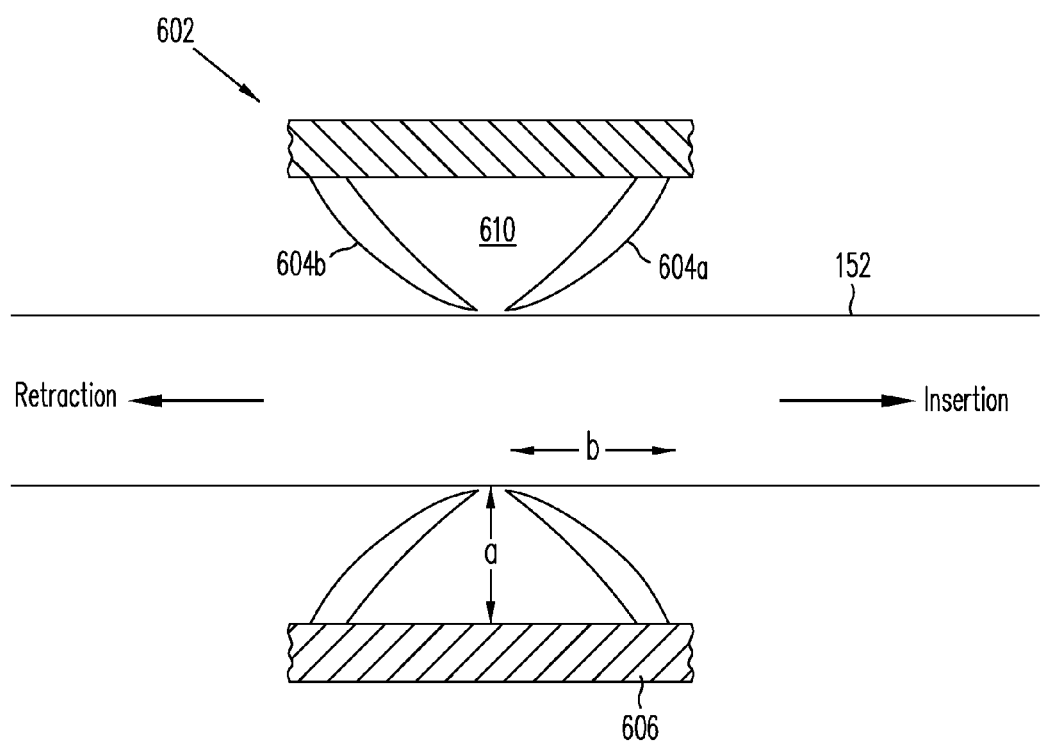

Lips 404a and 404b can be placed in a range of positions with respect to one another and may be substantially identically constructed. They may be separated from each other by a range of distances and may be oriented so that the seal lips point toward each other as shown in FIGS. 6A and 6B rather than away from each other as shown in FIGS. 4A and 4B. The frictional force resulting from seal 402 with lips 404a and 404b may be substantially symmetrical, however insufflation pressure inside the body will load lip 404a greater than lip 404b. As a result, with the embodiment illustrated in FIG. 4B, there may be a difference in the frictional force experienced depending on insertion or retraction of shaft 152.

Lips 404a and 404b can be characterized by the parameters b and a. In this case, b is the axial distance from where seal lip 404a or 404b connects to base 406 of seal 402 to where seal lip 404a or 404b contacts a wall of shaft 152. Then a is the radial distance from where seal lip 404a or 404b connects to base 406 of seal 402 to the wall of shaft 152 when seal 402 is engaged by shaft 152. A longer b will provide more radial compliance and maintain sealing contact with the wall of shaft 152 with less force variation over a greater range of eccentric misalignment of the seal 402 and the shaft 152. Longer b may also provide a higher loading effect from insufflation, for example. Longer b may also provide a better seal. A smaller dimension a results in a reduced moment arm for insertion friction forces between the seal lips 404a and 404b and shaft 152. This means that there is less increase in the lip contact force with shaft 152 and less self-amplification of the friction force in the direction of motion opposite the orientation of a seal lip.

It is possible to alter the seal lip dimension b of one of seal lips 404a and 404b to compensate for the unequal effect of insufflation pressure on the friction force of identical oppositely facing seal lips. For example, if dimension b is made slightly less for seal lip 404a than for seal lip 404b then the insufflation pressure induced increase in seal friction on seal lip 404a can be reduced so that the summed seal lip friction forces are equal in both directions of motion. This will further improve the ability to reduce seal friction induced errors in the estimated insertion axis tissue forces to be fed back to the surgeon through MTM's 122.

Friction in seal 402 can be reduced by lubrication as discussed above. Furthermore, friction in seal 402 can be reduced by texturing lips 404a and 404b, for example by providing a pebbled or rounded surface texture to lips 404 and 406. Textured surfaces may provide less friction while also providing a good seal between lips 404a and 404b and the wall of shaft 152. Lubrication such as parylene can be applied to seal 402 in order to reduce friction. Reduction in the friction along the insertion direction can help to provide more accurate force calculations by reducing the size of the friction correction to the sensor measured force and, if there is any asymmetry remaining in the frictional force, reducing the error in that correction.

The embodiments of seal 402 shown in FIGS. 4A and 4B are examples of a seal according to the present invention. Embodiments of the present invention provide symmetric sealing in that the insertion and retraction frictional forces are substantially the same. Although insufflation may cause some asymmetry in the frictional force to remain, that asymmetry will be within the range that still results in reliable force feedback to the surgeon or, in some embodiments, seal 402 may be modified such that the frictional forces on insertion and retraction are closer to being the same. In that fashion, the frictional forces can be predictable and subtracted from sensor measured forces in a calculation of the forces applied to shaft 152 so that a surgeon sitting at console 120 can have a reliable feedback of forces applied to shaft 152.

Figure 5A:
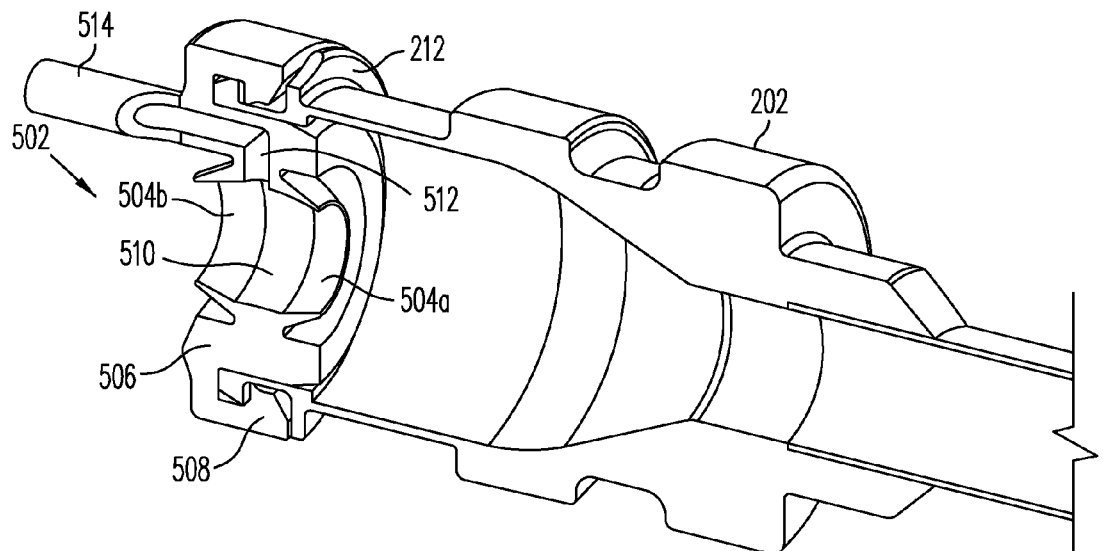
FIGS. 5A and 5B illustrate a cannula seal according to some embodiments of the present invention.
Figure 5B:
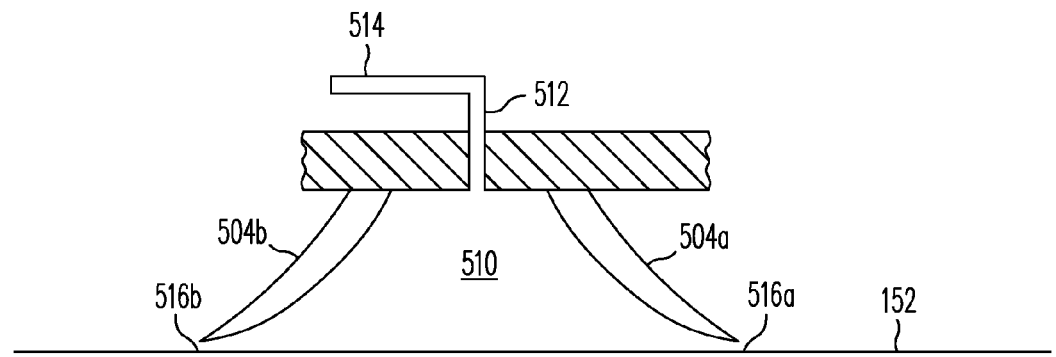
Figure 5B:
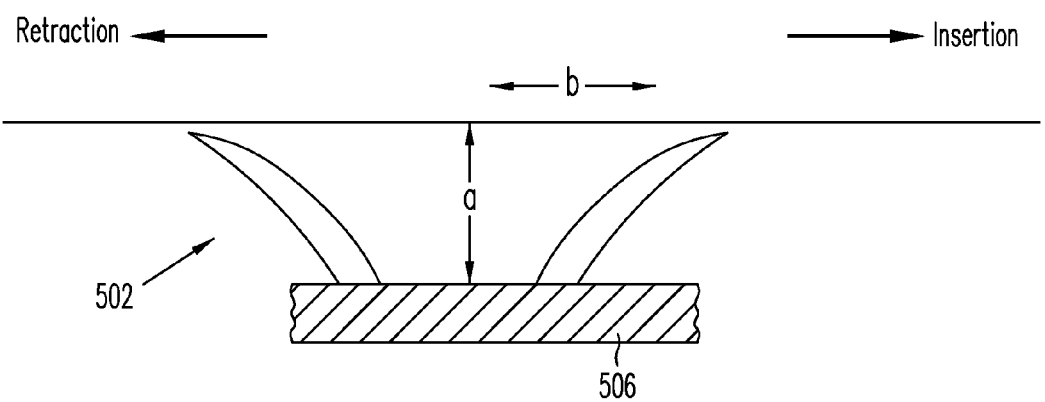

FIGS. 5A and 5B illustrate another embodiment of seal 902, a seal 502. As illustrated in FIG. 5A, seal 502 includes a hose connection 514 and a channel 512 that provides pressurized fluid to an annular cavity 510 that is formed between lips 504a and 504b and surrounding shaft 152. The pressurized fluid applied to cavity 510 can include $CO_2$, saline solution, air, or other fluids. During surgery, the abdomen of the patient may be inflated with pressurized $CO_2$ in order to provide more room in the surgical area for the surgical instruments. If $CO_2$ is provided at into cavity 510 at a pressure greater than that of the pressure in the surgical area, then lips 504a and 504b can be lifted from the wall of shaft 152 to form gaps 516a and 516b, respectively. In gaps 516a and 516b, a pressure seal can be formed. One advantage of forming such a pressure seal is that the frictional forces between seal 502 and shaft 152 are substantially eliminated. Further, such a pressure seal effectively prevents fluids from leaking around shaft 152 during the surgery due to the overpressure in annular cavity 510 with respect to the insufflation pressure in the patient's body. Pressurized $CO_2$ supplied to hose connection 514 can, for example, be provided through a separate regulator from a pressurized tank that is also utilized to provide pressurized $CO_2$ to the surgical area. In that case, the $CO_2$ pressure is set higher than the pressure of $CO_2$ to the surgical area in order to provide the pressure seal.

The pressure seal formed at gaps 516a and 516b allows the frictional force to be nearly zero. In some embodiments, cavity 510 is unpressurized, so that lips 504a and 504b can contact the wall of shaft 152 and provide a contact seal. Unpressurized, the frictional force supplied by the embodiment of seal 502 shown in FIG. 5B is substantially symmetric and can be lessened with the use of a lubricant. In some embodiments, lips 504a and 504b may have an inner diameter greater than the diameter of shaft 152 to that lips 504a and 504b do not fully contact shaft 152 even when cavity 510 is unpressurized although pressure greater than the insufflation pressure may still be applied to cavity 510 to prevent leakage of fluid from the insufflated surgical area. In this case, the fluid pressure may cause the inner surfaces of the lips to act as a fluid bearing with nearly zero friction against shaft 152.

FIGS. 6A and 6B illustrate another embodiment of seal 902, a seal 602 that includes an opposite approach. Seal 602 includes a base portion 606 and a seal portion 604. As shown in FIG. 6A, seal portion 604 includes symmetric seal lips 604a and 604b. Symmetric seal lips 604a and 604b contact the outer wall 152 in a symmetrical fashion and provide substantially symmetrical frictional forces along shaft 152 with respect to direction of motion. A cavity 610 may provide flexibility of seal members 604, resulting in a more compliant seal between seal members 604 and shaft 152. As discussed above, in some embodiments the frictional force may be lessened with the use of a lubricant.

Figure 6C:
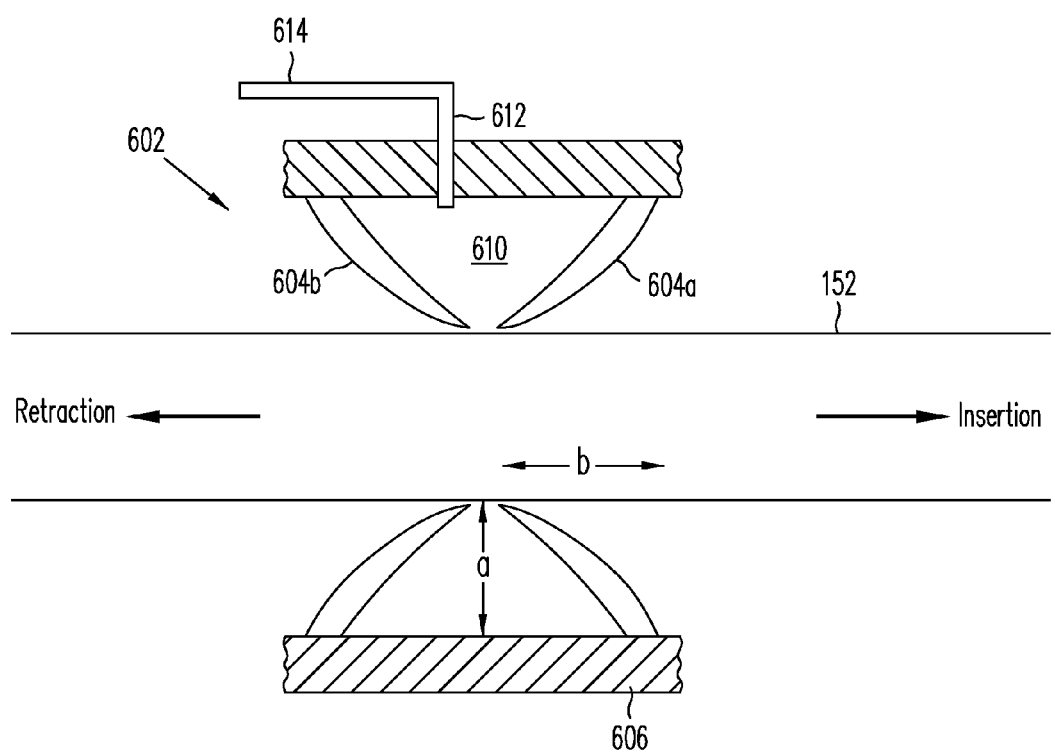

FIG. 6C illustrates another embodiment of seal 602. As shown in FIG. 6C, seal 602 may include a channel 612 and a hose connection 614 so that pressurized fluid may be utilized to pressurize cavity 610. Seal 602 may have an initial diameter clearance with respect to shaft 152 to insure minimum initial friction. As shown in FIG. 6C, pressurizing cavity 610 may help lips 604a and 604b to controllably engage the wall of shaft 152 sufficiently to insure a seal while still reducing friction compared to a seal designed for initial diameter interference with shaft 152. The elevated pressure in space 610 above the pressure in the patient's body cavity further aids the sealing effect because gas cannot flow from the lower pressure in the patient's body toward the higher pressure in seal cavity 610 adjacent the shaft 152.

Again in the embodiment illustrated in FIGS. 6A, 6B, and 6C in some embodiments an asymmetric frictional force caused by insufflation gas lifting lip 604a from shaft 152 may be compensated for by adjusting the dimensions of lips 604a and 604b accordingly. Further, frictional forces may be reduced with lubrication or by providing a textured surface on lips 604a and 604b where shaft 152 is contacted.

Figure 7A:
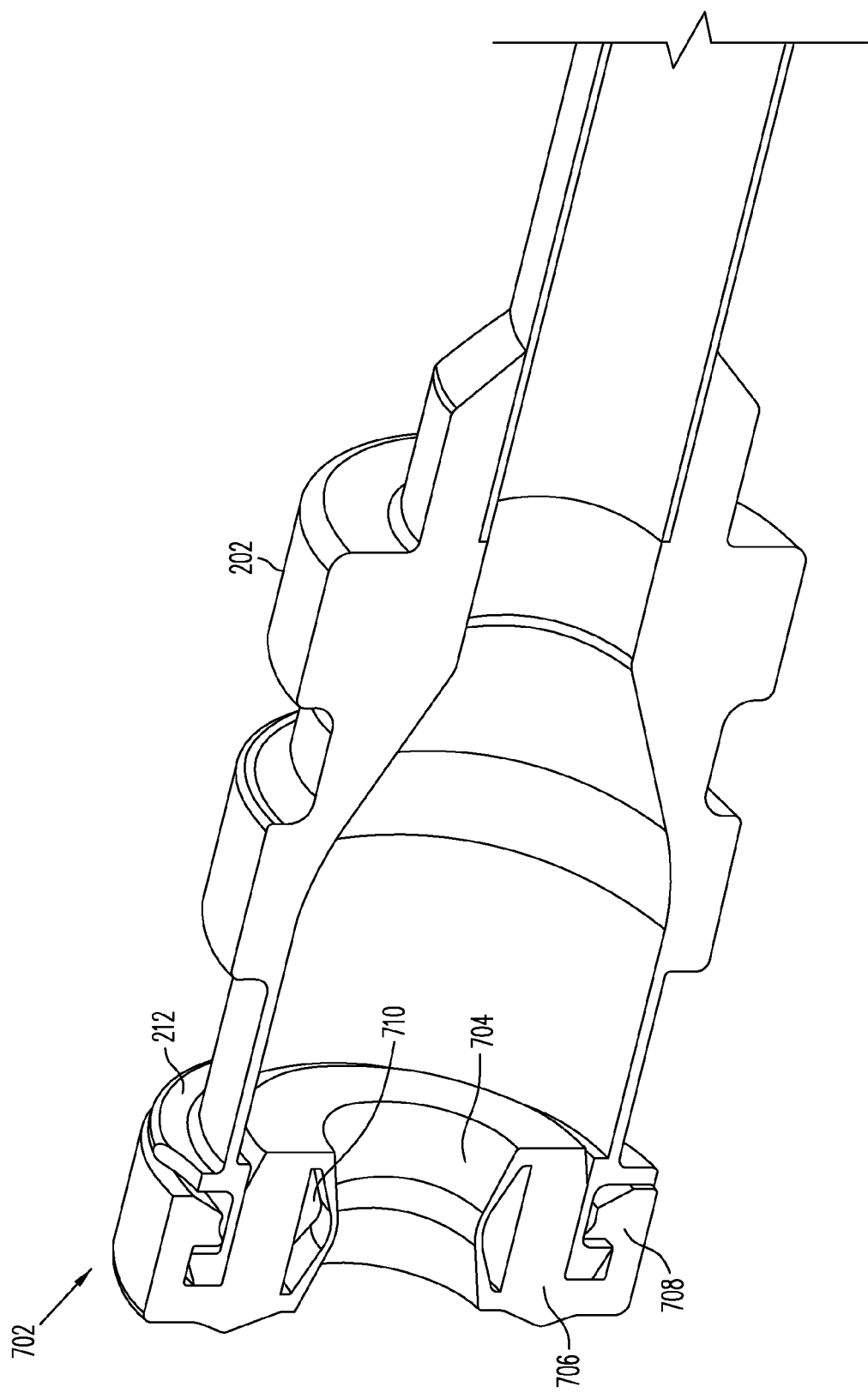
FIGS. 7A, 7B, and 7C illustrate cannula seals according to some embodiments of the present invention.
Figure 7B:
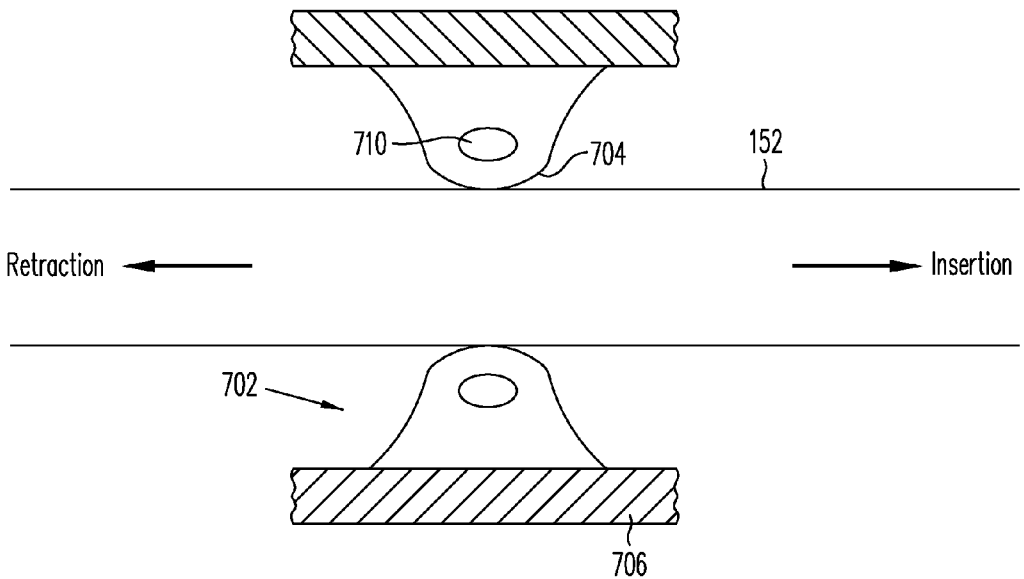

FIGS. 7A and 7B illustrate another embodiment of seal 902, a seal 702 that includes another approach. Seal 702 includes a base portion 706 and a seal portion 704. As shown in FIG. 7A, seal portion 704 provides a symmetric radially compliant seal surface. The symmetrical seal surface 704 contacts the outer wall 152 and provides substantially equal frictional forces along shaft 152 independent of motion direction. A cavity 710 provides radial flexibility of seal member 704, resulting in a more compliant seal between seal member 704 and shaft 152. As discussed above, in some embodiments the frictional force may be lessened with the use of a lubricant such as a grease or a pebble textured seal surface.

Figure 7C:
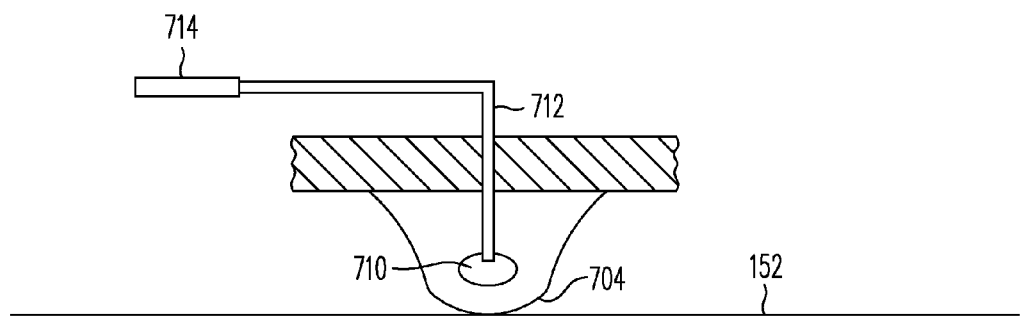
Figure 7C:
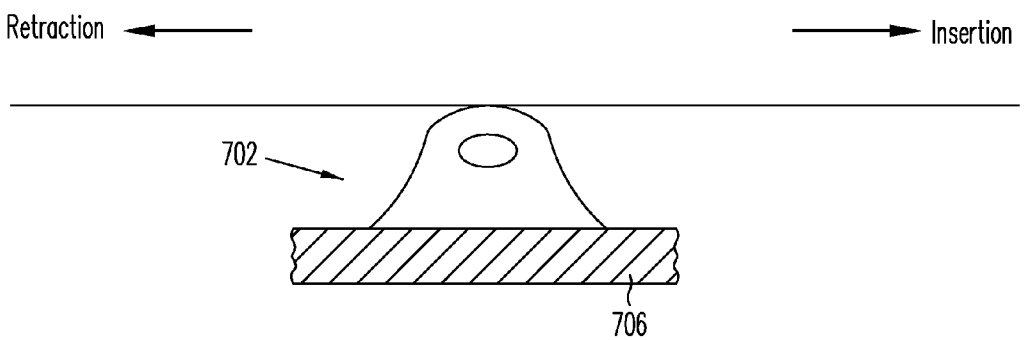

FIG. 7C illustrate an embodiment of seal 702 where cavity 710 can be pressurized. As shown in FIG. 7C, a channel 712 and hose connection 714 can be utilized to pressurize cavity 710. Seal 702 may be designed with initial diameter clearance with respect to shaft 152 to insure minimum initial friction. Pressurizing cavity 710 can help seal surface 704 controllably engage the wall of shaft 152 to provide sufficient contact force for adequate seal without excessive contact force that may provide unacceptable frictional forces on shaft 152.

In each of the embodiments of seal 902 (seals 402, 502, 602, and 702), seal surfaces 404, 504, 604 and 704, respectively, and shaft 152 can be coated with a lubricant such as Parylene. Parylene substantially lowers any remaining friction and exhibits almost no stiction (e.g., no difference between static friction and dynamic friction). Other lubricants, for example medical grade petroleum based lubricants or silicone based lubricants, can be utilized. Further, as discussed above, texturing of seal member 404, 504, 604 and 704 or shaft 152 may also lower the frictional force.

Figure 8A:
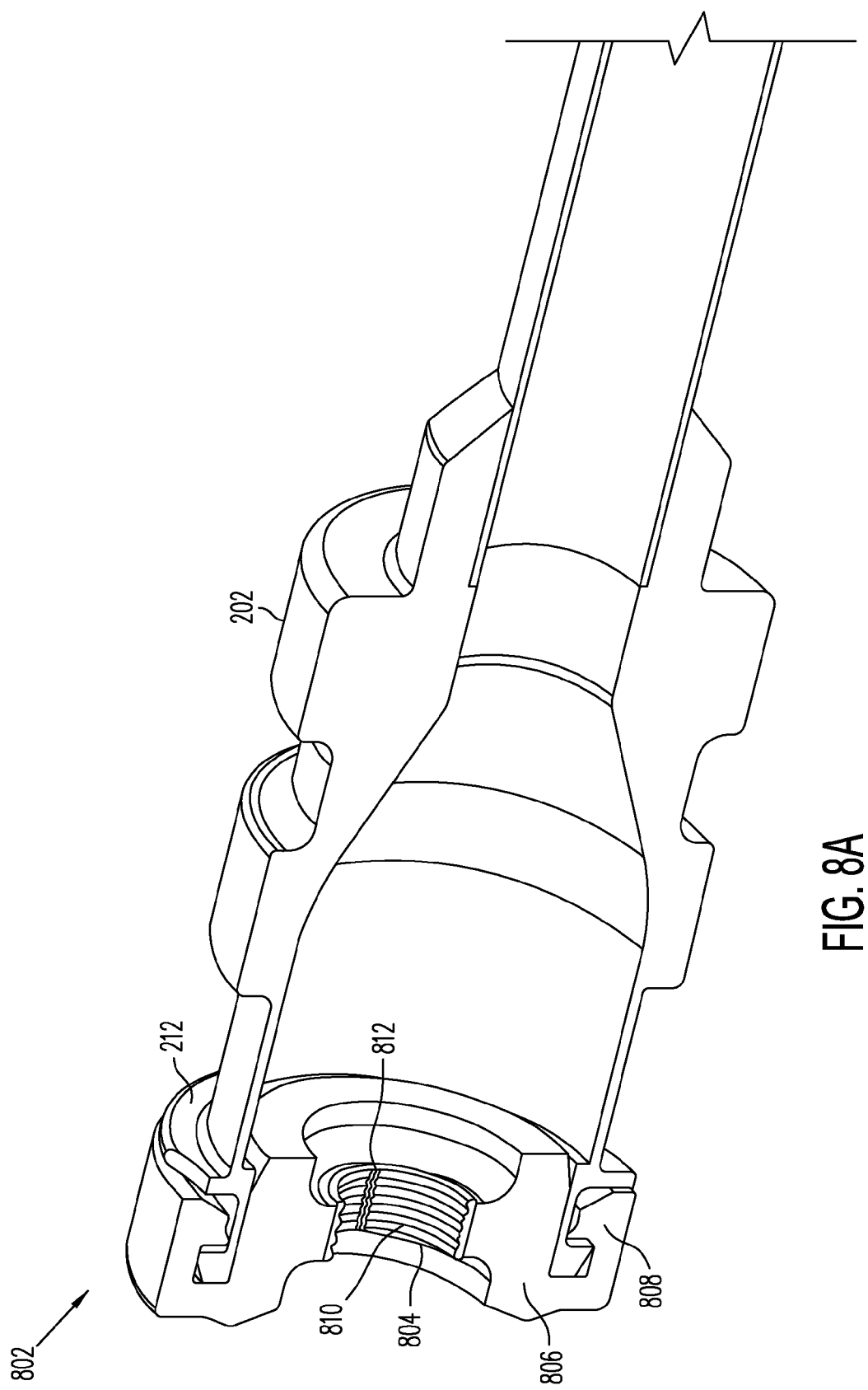

FIGS. 8A and 8B illustrate another embodiment of seal 902, a seal 802, that includes another approach. Seal 802 includes a base portion 806 and a seal portion 804. As shown in FIG. 8A, seal portion 804 provides a symmetric radially compliant seal surface. The symmetric circumferentially grooved cylindrical seal surface of 804 contacts the outer wall of shaft 152 and provides substantially equal frictional forces along shaft 152 independent of motion direction. Seal portion 804 may be made of a low friction polymer material such as PTFE insert molded or otherwise retained inside an elastomer seal body 802. Grooves 810 improve the sealing characteristics of the smooth lip-less seal design. A gap 812 permits a close fit without binding or excessive friction between the seal portion 804 and instrument shaft surface 152 in the case of tolerance variations in the respective diameters. Gap 812 can be any opening, for example a longitudinal or helical opening, intersecting grooves 810. The compliant elastomer material of seal 802 helps portion 804 conform to shaft 152 for the best seal. In some embodiments, grooves 810 may be pressured as discussed above.

Figure 9B:
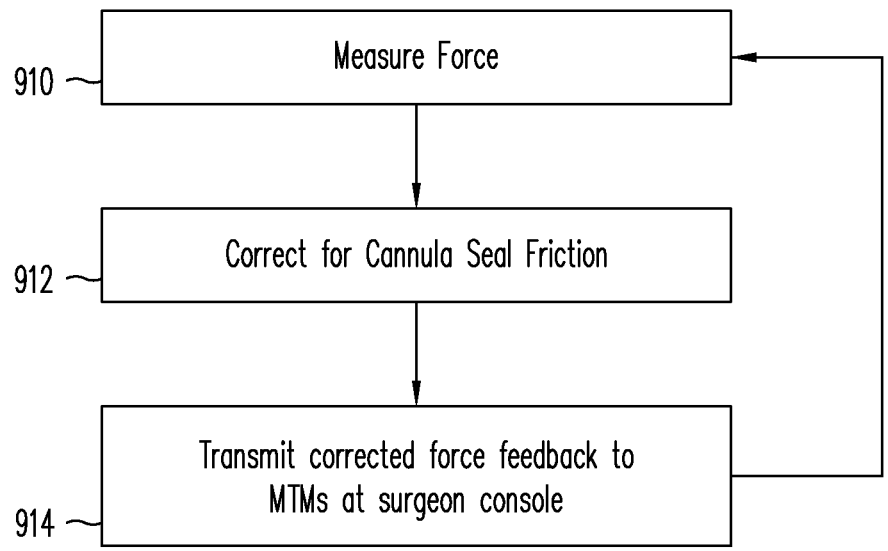

FIGS. 9A and 9B illustrate measurement of the insertion force in order to provide feedback to a surgeon utilizing MTMs 122 at console 120. As shown in FIG. 9A, cannula seal 902, which may be one of seals 402, 502, 602, 702, or 802) according to some embodiments of the present invention is attached to cannula 202. As such, cannula seal 902 exhibits substantially symmetric frictional forces with regard to both the insertion and retraction directions. Shaft 152 extends through cannula 202 so that cannula seal 902 engages shaft 152 as discussed above and end effector 206 is exposed. A force sensor 904 is coupled with instrument interface 150 or mounted on instrument arm 106. Force sensor 904 communicates force readings to data processing unit 142, which computes the force feedback to apply to MTM 122 of surgeon's console 120. Force sensor 904 can be any device capable of detecting the axial force applied to shaft 152, for example a conventional strain gage force transducer, a piezoelectric element, an optical fiber strain gauge, or other device.

Figure 9C:
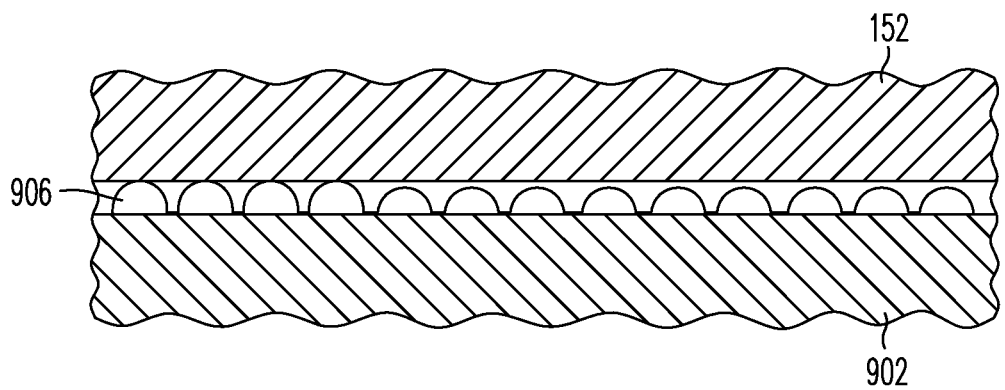
FIG. 9C illustrates a surface contact between a seal as shown in FIG. 9A and an instrument shaft.

FIG. 9C illustrates a surface contact between seal 902 and a shaft 152 according to some embodiments of the invention. As discussed above, seal 902, which can be one of seals 402, 502, 602, 702, and 802, can be formed of silicone rubber. Other materials that can be utilized to form seal 902 can include medical grades of urethane, Pebax, EPDM, Viton, or other TPE and rubber compounds as well as low friction polymers such as PTFE. Seal 902 according to some embodiments of the present invention, can be disposable and can be attached to cannula 202 for the duration of a single surgery. As has been discussed above, seal 902 can be coated with a lubricant such as parylene to reduce frictional forces along the insertion/retraction direction. As is illustrated in FIG. 9C, some embodiments of seal 902 may include a textured surface 906 that engages the inside wall of shaft 152. Textured surface 906 can help to reduce the frictional forces between seal 902 and shaft 152.

FIG. 9B illustrates an algorithm for processing the force data from force sensor 902. As shown in FIG. 9B, a force measurement is taken by force sensor 904 in step 910. In step 912, the force measurement is corrected for cannula seal friction. In step 912, the cannula seal friction utilizing a cannula seal 902, which can be one of seals 402, 502, 602, 702, 802, according to some embodiments of the present invention can be predictable. In some embodiments, the cannula seal friction can be symmetric with respect to insertion and retraction direction. In some embodiments, the cannula seal frication can be substantially zero. In step 914, the corrected force is utilized to provide haptic feedback to the surgeon at console 122, for example by applying a resistance force to the motion of a MTM 122.

The above detailed description is provided to illustrate specific embodiments of the present invention and is not intended to be limiting. Numerous variations and modifications within the scope of the present invention are possible. The present invention is set forth in the following claims.

What is claimed is:

1. A cannula seal, comprising:
a base portion that engages with a cannula, the base portion including an inner wall defining an interior space sized and shaped to receive an instrument shaft;

a seal portion coupled with the base portion, the seal portion including at least a first lip and a second lip, the first lip extending inwardly and distally from the inner wall of the base portion to a first lip edge in the interior space, and the second lip extending inwardly and proximally from the inner wall of the base portion to a second lip edge in the interior space, the first lip edge and second lip edge being separated by a gap a fluid channel extending through the base portion to a fluid channel exit in the inner wall of the base portion between the first lip and the second lip;

the first lip and second lip being sized and shaped to slidably seal against an outer surface of the instrument shaft inserted into the interior space.

2. The seal of claim 1, wherein the first lip and the second lip are sized and shaped to engage the instrument shaft in symmetrically opposing directions.

3. The seal of claim 2, wherein the first lip is oriented in an insertion direction and the second lip is oriented in a retraction direction that is opposite the insertion direction, such that the first lip provides a lower friction against the instrument shaft than the second lip as the instrument shaft is moved in the insertion direction, and the second lip provides a lower friction against the instrument shaft than the first lip when the instrument shaft is moved in the retraction direction.

4. The seal of claim 2, wherein the first lip and the second lip are shaped differently from one another.

5. The seal of claim 1, wherein the second lip is oriented in an insertion direction and the first lip is oriented in a retraction direction that is opposite the insertion direction, such that the second lip provides a lower friction against the instrument shaft than the first lip as the instrument shaft is moved in the insertion direction, and the first lip provides a lower friction against the instrument shaft than the second lip when the instrument shaft is moved in the retraction direction.

6. The seal of claim 1, wherein the friction between the seal portion and the instrument shaft is adjusted by delivering pressurized fluid through the fluid channel exit to the interior space.

7. The seal of claim 6, wherein the pressurized fluid is chosen from a set of fluids consisting of $CO_2$, air, and saline solution.

8. The seal of claim 7, wherein the first lip and the second lip do not engage the shaft when the fluid channel is unpressurized.

9. The seal of claim 6, wherein the seal is situatable in an incision in a patient's body, and wherein when an insufflation pressure is delivered in the patient's body and a pressurized fluid is delivered to the fluid channel, a seal between at least one of the first lip and second lip and the outer surface of the instrument shaft is formed by an overpressure relative to the insufflation pressure.

10. The seal of claim 1, wherein the seal portion includes a symmetric radially compliant seal surface.

11. The seal of claim 10, wherein the symmetric radially compliant seal surface engages the outer surface of the instrument shaft.

12. The seal of claim 10, wherein the first lip and second lip are sized and shaped such that an insertion frictional force between the seal portion and the instrument shaft experienced during insertion of an instrument shaft through the seal and into a patient's body is substantially symmetrical and substantially equal to a retraction frictional force between the seal portion and the instrument shaft experienced during retraction of an instrument shaft through the seal.

13. The seal of claim 12, wherein the first lip is on an external side of the cannula seal and the second lip is on a body side of the cannula seal, the second lip being exposed to insufflation pressure when the seal is situated in an incision in a body and insufflation pressure is delivered to the body, the second lip being sized sufficiently differently than the first lip to compensate for forces from insufflation pressure acting on the second lip.

14. The seal of claim 1, wherein the seal portion includes a lubricant coating.

15. The seal of claim 14, wherein the lubricant is parylene.

16. The seal of claim 1, wherein the seal portion includes a textured surface that engages the instrument shaft.

17. A method of symmetrically sealing a cannula, comprising:
slidably engaging an instrument shaft within an interior space of a cannula seal;
delivering a pressurized fluid through the seal to the interior space of the cannula seal slidably engaged with an instrument shaft to bias at least two discrete lips on the cannula seal against the instrument shaft and slidably seal the lips against the instrument shaft; and
changing friction between the lips and the shaft by adjusting the pressure of the pressurized fluid in the interior space.

18. The method of claim 17, wherein delivering a pressurized fluid through the seal to the interior space to bias at least two discrete lips on the cannula seal includes delivering a pressurized fluid between first lip and a second lip, the first lip and the second lip being placed to engage the instrument shaft in symmetrically opposing directions.

19. The method of claim 18, wherein a seal between the lips and the outer surface of the instrument shaft is formed by an overpressure in the interior space relative to an insufflation pressure in a patient's body.

20. The method of claim 17, wherein delivering a pressurized fluid biases at least one radially compliant seal surface against the instrument shaft.

21. The method of claim 17, further comprising coating at least a portion of the at least two discrete lips with a lubricant.

22. The method of claim 21, wherein the lubricant is parylene.

23. A surgical system, comprising:
a controller;
an arm coupled to the controller;
a surgical instrument coupled to the arm and controlled by the controller, the surgical instrument including an instrument shaft and a force sensor;
a cannula receiving the instrument shaft of the surgical instrument; and
a cannula seal attached to the cannula and engaging the instrument shaft of the surgical instrument, the cannula seal including a base portion that engages with the cannula, a fluid channel formed in the base portion and in communication with an interior space in the cannula seal, and a seal portion integrally formed with the base portion, the seal portion having a first lip and a second lip, the first lip extending into the interior space in the cannula seal and terminating at a first lip edge, the second lip extending into the interior space and terminating at a second lip edge, the first lip edge being spaced from the second lip edge to define a gap, the first lip and second lip slidably engaging with the instrument shaft such that an insertion frictional force between the seal portion and the instrument shaft is substantially symmetrical and substantially equal with a retraction frictional force, wherein the cannula seal is configured to allow pressurized fluid to be delivered to the interior space through the fluid channel sufficient to adjust the insertion frictional force and the retraction frictional force, and wherein the controller executes code that receives force measurements from the force sensor, corrects the force measurements for friction between the cannula seal and the instrument shaft, and transmits corrected force feedback to a master tool manipulator via the controller.

* * * * *